US00PP35778P2

(12) United States Plant Patent
Olesen

(10) Patent No.: US PP35,778 P2
(45) Date of Patent: Apr. 30, 2024

(54) ROSE PLANT NAMED "POULVIC010"

(50) Latin Name: *Rosa hybrida*
Varietal Denomination: Poulvic010

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/445,483

(22) Filed: Sep. 8, 2023

(30) Foreign Application Priority Data

Sep. 30, 2022 (QZ) ..... PBR 2022/2179

(51) Int. Cl.
*A01H 5/02* (2018.01)
*A01H 6/74* (2018.01)

(52) U.S. Cl.
USPC ..... Plt./121

(58) Field of Classification Search
USPC ..... Plt./101, 116, 121
See application file for complete search history.

*Primary Examiner* — Karen M Redden

(57) ABSTRACT

A new rose plant of the Miniature class which has abundant, pink flowers and attractive foliage. This new and distinct variety has shown to be uniform and stable in the resulting generations from asexual propagation.

2 Drawing Sheets

Botanical designation: *Rosa hybrida.*
Variety denomination: 'Poulvic010'.

This application claims priority to Plant Breeder's Rights Application Number 2022/2179, which was filed at the Community Plant Variety Rights Office in the European Union on Sep. 26, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2017 and the resulting seeds were planted in a controlled environment in Fredensborg, Denmark. The new variety, named 'Poulvic010', originated as a single seedling from the stated cross.

The new variety may be distinguished from its male pollen parent and female seed parent primarily by the following characteristics. The male pollen parent plant has white flowers while the new variety has pink flowers. The female seed parent plant has pink flowers about 60 mm in diameter flowers while the new variety has pink flowers 95 mm in diameter.

The objective of the hybridization of this rose variety was to create a new and distinct variety with unique qualities, such as:

1. Uniform and abundant pink flowers which are large for a miniature;
2. Vigorous, but very compact growth when propagated on its own roots;
3. Exceptional disease resistance.

This combination of qualities is not present in previously available commercial cultivars of this type, known to the inventor, and distinguish 'Poulvic010' from all other varieties of which we are aware.

As part of the rose development program, Mogens N. Olesen germinated the seeds from the aforementioned hybridization during winter of 2017 and conducted evaluations on the resulting seedlings in a controlled environment in Fredensborg, Denmark. 'Poulvic010' was selected in the spring of 2018 by the inventor as a single plant from the progeny of the aforementioned hybridization.

Asexual reproduction of 'Poulvic010' by rooted cuttings was first done by Mogens N. Olesen in the nursery in Fredensborg, Denmark in July, 2018. This initial and other subsequent asexual propagations conducted in controlled environments have demonstrated that the characteristics of 'Poulvic010' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulvic010'.

Specifically illustrated in FIG. 1 of the drawings are a fully open flower viewed from above showing peak diameter, a cluster of partially open flowers on the branch showing multiple blooms on a branch, flower petals detached, and sepals detached revealing reproductive flower parts.

Figure 1:
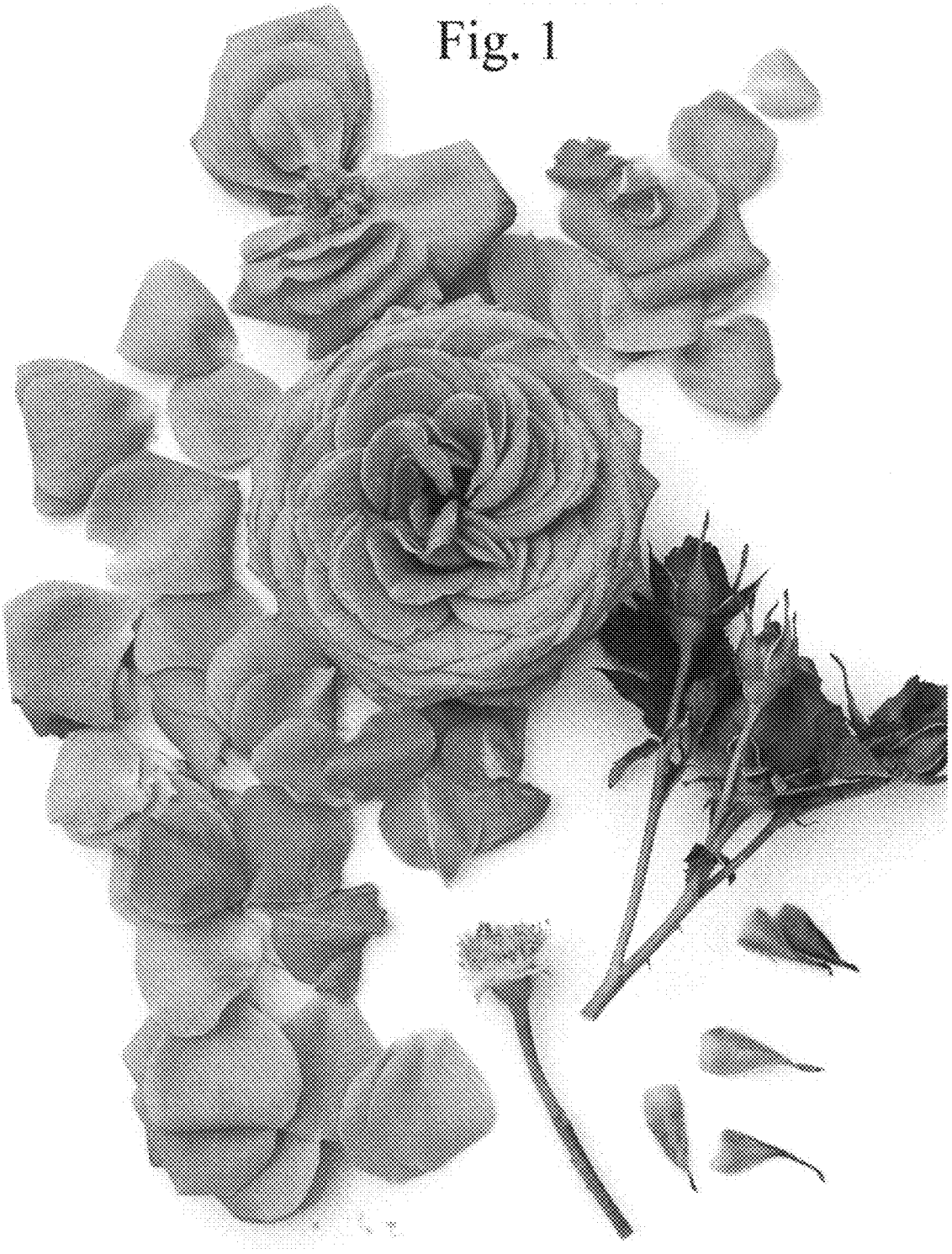
Figure 2:
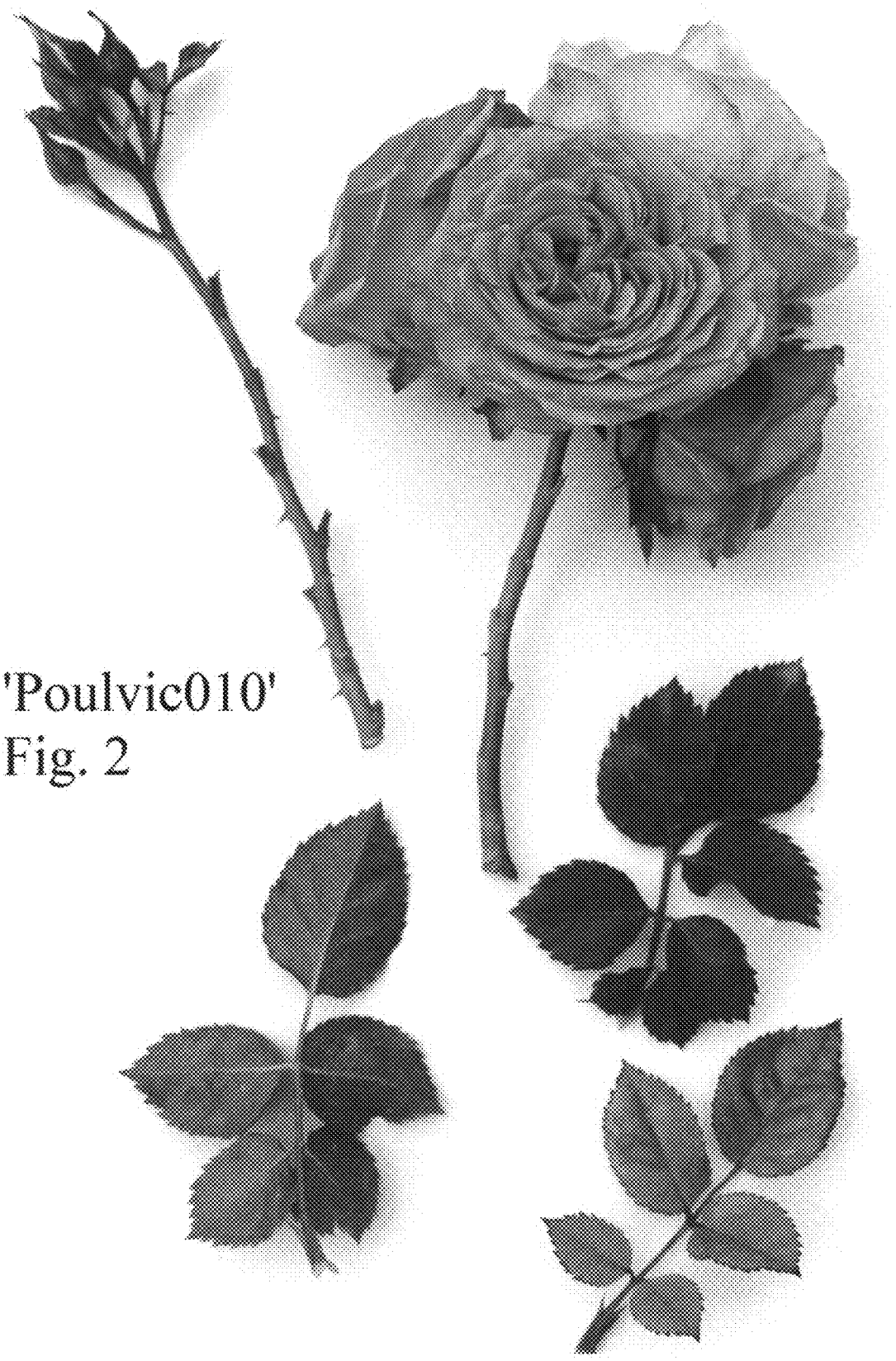

Specifically illustrated in FIG. 2 of the drawings are open flowers on a branch, bare juvenile stem exhibiting anthocyanin, juvenile and mature leaves. Plants shown are 15 months in age.

DETAILED DESCRIPTION OF THE VARIETY

The following is a description of 'Poulvic010', as observed in its growth in an outdoor nursery in Half Moon Bay, California. Observed plants are 15 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulpal036', U.S. Plant Pat. No. 24,635 are compared to the claimed plant. While 'Poulvic010' has 85 flower petals, 'Poulpal036' has 65 flower petals. The claimed plant has a flower diameter of 95 mm while 'Poulpal036' has a flower diameter of 85 to 90. Open flowers of 'Poulvic010' are generally Red-Purple Group 68B in color while 'Poulpal036' has a general tonality of Red-Purple Group 58C. The comparison variety has a moderate floral scent, while 'Poulvic010' has strong perfume.

FLOWER AND FLOWER BUD

Blooming habit: Continuous.

Flower bud:

- *Size.*—Upon opening, 27 mm in length from base of receptacle to end of bud. Bud diameter is 18 mm.
- *Bud form.*—Ucerolate.
- *Bud color.*—As sepals divide petals are Red-Purple Group 60A and Red-Purple Group N57B.
- *Sepal inner surface.*—Color: Yellow-Green Group 144A. Surface: Lightly pubescent.
- *Sepal outer surface.*—Color: Yellow-Green Group 144A with intonations of Greyed-Purple 187B on margins. Texture: Smooth.
- *Sepal shape.*—Apex: Cirrhose. Base: Flat at union with receptacle.
- *Sepal margin.*—Margins have very weak foliaceous appendages on three of the five sepals.
- *Sepal size.*—26 mm long, 10 mm wide.
- *Receptacle.*—Texture: Smooth. Size: 10 mm in height, 10 mm wide. Color: Yellow-Green Group 144A. Shape: Campanulate.
- *Pedicel.*—Surface: Smooth. Length: 15 mm. Diameter: 4 mm on average. Color: Yellow-Green Group 144A with intonations of Greyed-Orange Group 163B. Strength: Strong.
- *Peduncle.*—Length: 2 to 4 cm. Diameter: About 3 mm. Color: Yellow-Green Group 145A with light intonations of Greyed-Orange Group 163B. Texture: Smooth.

Flower bud development: Flower buds are borne in single or in clusters up to 5 flower buds per stem.

Flower bloom:

- *Fragrance.*—Strong perfume.
- *Duration.*—The blooms have a duration on the plant of approximately 19 days. Petals fall cleanly away from plant after flowers have fully matured.
- *Size.*—Flower diameter is 95 mm when open. Flower depth is 43 mm.
- *Flower shape.*—Rosette, very double flower with many slightly overlapping petals of different sizes.
- *Shape of flower, side view.*—The upper portion is flat. The lower portion is deep concave.

Petalage: Under normal conditions, flowers have about 85 petals.

General tonality of flower: Open flowers are Red-Purple Group 68B.

Petal color:

- *Upon opening, outer petals.*—Upper surface: Red-Purple Group 68B. Lower surface: Red-Purple Group 67B at marginal zone. At basal zone Red Group 55B.
- *Upon opening, inner petals.*—Upper surface: Red Group 52B with a Yellow Group 7D petal spot. Lower surface: Red Group 52C. Basal zone Yellow Group 8B.
- *Basal petal spots, upon opening.*—Upper surface: Yellow Group 8D. Lower surface: Green-White Group 157C.

Petals:

- *Petal reflex.*—Somewhat reflexed.
- *Margin.*—Entire and uniform. Moderate undulations.
- *Shape.*—Broad and rounded. Apex shape: Rounded. Base shape: Acute.
- *Size.*—45 mm (l)×45 mm (w).
- *Texture.*—Smooth.
- *Thickness.*—Average.

Petaloids:

- *Size.*—12 mm (l) by 9 mm (w).
- *Quantity.*—About 12.
- *Shape.*—Elliptical with an acute base and rounded apex.
- *Color.*—The upper side is Red Group 52B with a Yellow Group 7D petaloid spot. The underside Red Group 52C, with a basal point of attachment Yellow Group 8B.

Reproductive flower parts:

- *Pollen.*—None observed.
- *Anthers.*—Size: 2 mm in length. Color: Yellow Group 13C. Quantity: 46 on average.
- *Filaments.*—Color: Yellow Group 8D. Length: 10 mm.
- *Pistils.*—Length: 4 mm. Quantity: 30 on average.
- *Stigmas.*—Color: White Group 155A.
- *Styles.*—Color: White Group 155A.
- *Location of stigmas.*—Inferior in location relative to the length of the filaments and the height of the anthers.
- *Hips.*—None Observed.

PLANT

Plant growth: Upright and well branched. Plants are 31 cm in height, and 37 cm wide.

Stems:

- *Color of juvenile growth.*—Yellow-Green Group 144B.
- *Color of mature growth.*—Yellow-Green Group 144A.
- *Length.*—Canes are about 13 cm from the base of the plant to the flowering portion.
- *Diameter.*—About 4 mm.
- *Internodes.*—On mature canes about 27 mm between nodes.
- *Surface texture.*—Young wood: Smooth. Older wood: Smooth.

Long prickles:

- *Incidence.*—10 prickles per 10 cm of stem.
- *Size.*—Average length of prickles on mature stems is 4 mm.
- *Shape.*—Upper portion is linear. Lower portion is concave.
- *Color.*—Juvenile prickles: Greyed-Red Group 181A. Mature prickles: Greyed-Orange Group 177D.

Plant foliage:

*Compound leaf.*—112 mm (l)×75 (w).

*Quantity.*—3 leaves per 10 cm of stem on average.

*Leaf bearing angle to the stem.*—45 degrees.

*Color of juvenile foliage.*—Upper side: Yellow-Green Group N144A with intonations of Greyed-Red Group 180B. Lower side: Yellow-Green Group 145B.

*Color of mature foliage.*—Upper side: Yellow-Green Group 147A. Lower side: Yellow-Green Group 146B.

Plant leaves and leaflets:

*Stipules.*—Size: 5 mm long, 3 mm wide. Quantity: 2 per compound leaf. Shape: Linear, slightly broad based with outward extending apex. Margins: Finely serrated. Color: Yellow-Green Group 144A.

*Petiole.*—Length: 10 mm. Diameter: 2 mm. Upper surface color: Yellow-Green Group 144A. Lower surface color: Yellow-Green Group 144A.

*Rachis.*—Length: About 44 mm. Upper surface color: Yellow-Green Group 144A. Lower surface color: Yellow-Green Group 144A.

*Leaflet.*—Quantity: Normally 5 leaflets. Margins: Serrated. Size: Terminal leaflets are about 51 mm long, 36 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulvic010' substantially as described and illustrated herein.

* * * * *

'Poulvic010'

'Poulvic010'